US011969516B2

(12) United States Patent
Fryer et al.

(10) Patent No.: US 11,969,516 B2
(45) Date of Patent: Apr. 30, 2024

(54) BIOLOGICAL INDICATOR FOR LIQUID-CHEMICAL STERILIZATION SYSTEM

(71) Applicant: ASP GLOBAL MANUFACTURING GMBH, Schaffhausen (CH)

(72) Inventors: Benjamin M. Fryer, Lake Forest, CA (US); Samuel J. Rhodes, Los Angeles, CA (US); Navid Omidbakhsh, Mission Viejo, CA (US); Cole G. Mcneal, Costa Mesa, CA (US); Masood H. Siddiqui, Irvine, CA (US)

(73) Assignee: ASP Global Manufacturing GMBH (CH)

( * ) Notice: Subject to any disclaimer, the term of this patent is extended or adjusted under 35 U.S.C. 154(b) by 1062 days.

(21) Appl. No.: 16/719,310

(22) Filed: Dec. 18, 2019

(65) Prior Publication Data

US 2020/0199517 A1 Jun. 25, 2020

Related U.S. Application Data

(60) Provisional application No. 62/782,931, filed on Dec. 20, 2018, provisional application No. 62/782,949, filed on Dec. 20, 2018.

(51) Int. Cl.
*A61L 2/18* (2006.01)
*A61L 2/28* (2006.01)
(Continued)

(52) U.S. Cl.
CPC .................. *A61L 2/18* (2013.01); *A61L 2/186* (2013.01); *A61L 2/28* (2013.01); *C12M 1/34* (2013.01);
(Continued)

(58) Field of Classification Search
CPC .............. A61L 2/18; A61L 2/28; C12M 37/06
See application file for complete search history.

(56) References Cited

U.S. PATENT DOCUMENTS

| 4,304,869 A | 12/1981 | Dyke |
| 5,073,488 A | 12/1991 | Matner et al. |
| (Continued) | | |

FOREIGN PATENT DOCUMENTS

| CN | 201581080 U | 9/2010 |
| EP | 1 025 258 B1 | 6/2005 |
| (Continued) | | |

OTHER PUBLICATIONS

Wiggens: Department of Health & Human Services, Jun. 20, 2017, Retrieved From the Internet: URL:http://wwwaccessdata.fda.gov/cdrh_docs/pdf17/K170039.pdf; p. 2, paragraphs 1-4, 10 pages.
(Continued)

*Primary Examiner* — Donald R Spamer
(74) *Attorney, Agent, or Firm* — Lerner David LLP (57) ABSTRACT

Disclosed herein are biological indicators suitable for use in a liquid-chemical sterilization process that may be conducted by an automated endoscope reprocessor. The biological indicator may include one or more ports for introducing and removing a liquid-chemical sterilant therefrom. The biological indicators may include features, such as a declivity leading to a port opening or a pipette, that may assist in transferring the liquid-chemical sterilant. The system may additionally include a holder having features that facilitate use of the system and biological indicators.

15 Claims, 10 Drawing Sheets

(51) Int. Cl.
*C12M 1/00* (2006.01)
*C12M 1/12* (2006.01)
*C12M 1/32* (2006.01)
*C12M 1/34* (2006.01)
*C12M 3/00* (2006.01)
*C12Q 1/22* (2006.01)

(52) U.S. Cl.
CPC ............ *C12M 23/12* (2013.01); *C12M 23/34* (2013.01); *C12M 23/38* (2013.01); *C12M 23/40* (2013.01); *C12M 23/48* (2013.01); *C12M 37/06* (2013.01); *C12Q 1/22* (2013.01); *A61L 2202/24* (2013.01)

(56) References Cited

U.S. PATENT DOCUMENTS

| | | | |
|---|---|---|---|
| 5,223,401 | A | 6/1993 | Foltz et al. |
| 5,418,167 | A | 5/1995 | Matner et al. |
| 5,921,256 | A | 7/1999 | Barin |
| 6,025,189 | A | 2/2000 | Bolea et al. |
| 9,322,046 | B2 | 4/2016 | Chandrapati et al. |
| 10,058,482 | B2 | 8/2018 | Haindl et al. |
| 10,444,050 | B2 | 10/2019 | Zhang et al. |
| 2003/0190256 | A1 | 10/2003 | Halstead et al. |
| 2008/0070272 | A1 | 3/2008 | Franciskovich et al. |
| 2012/0186201 | A1 | 7/2012 | Clouser et al. |
| 2017/0246330 | A1 | 8/2017 | Lyon |
| 2017/0253845 | A1 | 9/2017 | Amin |
| 2018/0187142 | A1 | 7/2018 | Truong |
| 2018/0245122 | A1 | 8/2018 | Soto et al. |
| 2019/0125912 | A1* | 5/2019 | Bommarito ............... A61L 2/26 |

FOREIGN PATENT DOCUMENTS

| | | |
|---|---|---|
| EP | 3 366 315 A1 | 8/2018 |
| JP | 2010-504101 A | 2/2010 |
| WO | 00/69475 A1 | 11/2000 |
| WO | 2005000364 A2 | 1/2005 |
| WO | 2012/088048 A1 | 6/2012 |
| WO | 2016/057520 A1 | 4/2016 |
| WO | 2018025207 A1 | 2/2018 |

OTHER PUBLICATIONS

PCT Notification of Transmittal of the International Search Report and the Written Opinion of the International Searching Authority, or the Declaration; International Application No. PCT/IB2019/061194; dated Jun. 24, 2020; 18 Pages.

* cited by examiner

BIOLOGICAL INDICATOR FOR LIQUID-CHEMICAL STERILIZATION SYSTEM

CROSS-REFERENCE TO CO-PENDING APPLICATION

The present application claims the benefit under 35 U.S.C. § 119 of U.S. Provisional Patent Application No. 62/782,931, filed Dec. 20, 2018 and of U.S. Provisional Patent Application No. 62/782,949, also filed Dec. 20, 2018. The entire contents of these applications are incorporated by reference herein in their entirety.

FIELD

The subject matter disclosed herein concerns apparatuses and techniques for assessing the adequacy of a liquid chemical sterilization routine, particularly as applied to endoscope sterilization.

BACKGROUND

Medical devices are typically sterilized before use to minimize the likelihood that a contaminated device might be used on a subject, which could cause an infection in the subject. Various sterilization techniques may be employed, such as steam, hydrogen peroxide, and vapor phase sterilization, either with or without a gas plasma and ethylene oxide (EtO).

Certain sterilization techniques are conducted at pressures other than ambient pressure or atmospheric pressure. For example the STERRAD® System, STERRAD® NX System or STERRAD® 100NX System of Advanced Sterilization Products, Division of Ethicon US, LLC, a Johnson & Johnson company, are examples of sterilization systems, or sterilizers, that vaporize hydrogen peroxide and operate at low pressures, e.g., less than 200 millitorr.

Various elongate medical devices having lumens, e.g., endoscopes, are challenging to sterilize by a vapor sterilant, e.g., vaporized hydrogen peroxide, for various reasons. For example, because pressure in a lumen decreases from the lumen's inlet as a function of length and diameter, the pressure drop must be overcome to ensure that sterilant passes through the entire lumen and reaches all surfaces of the lumen. Further, lumens may collect debris or be blocked by fluids, such as rinse water.

Often vapor-based sterilization routines incorporate a sterilization indicator, such as a biological indicator or a chemical indicator, which may provide an indication of the effectiveness of a sterilization cycle. Even though such indicators may be positioned close to an endoscope in a sterilization chamber, they may not be reliable for assessing the sterility of the endoscope because the portions of the endoscope that are most difficult to sterilize are typically deep within the endoscope's lumens.

SUMMARY OF THE DISCLOSURE

Disclosed herein is a biological indicator suitable for use in a liquid-chemical sterilization process. The biological indicator may include a vial and a cap disposed atop the vial. A first port (or vial port) may be disposed through a base of the vial, and a second port, (or cap port) may be disposed through the cap. An exhaust port may also be disposed through the cap. The cap may additionally include a wing extending therefrom.

A first valve may be disposed in the first port and a second valve may be disposed in the second port. Further, a carrier impregnated with microorganisms may be disposed in the vial.

The first port may include an opening disposed inside the vial and a bottom portion of the vial may include a declivity directed toward the opening. In such embodiments, the carrier may be disposed above the opening and in contact with the declivity. Further the carrier may include a void disposed therethrough.

A pipette may be connected to the port in the cap. Where the pipette is included, the vial may optionally not include a vial port. As such, the pipette may include a first end connected to the cap port and a second end disposed proximate to the base of the vial.

The biological indicator may also include an ampule containing a growth medium that is disposed at least partially within the vial. An insert may be disposed in the vial to contact or support the ampule. The ampule may include an irregular cross-sectional shape such that the pipette may be disposed in an indent defined by the irregular cross-sectional shape.

A liquid-chemical sterilization system is also described herein. This system may include a biological indicator that has a housing defining an interior and including a first port having a first valve and a second port having a second valve. A divider may be disposed within the interior, between the first port and the second port, to define two chambers. A carrier impregnated with microorganisms may be disposed in one of the two chambers. The system may also include a source of a liquid-chemical sterilant and a first fluid-delivery component connected to the source of the liquid-chemical sterilant. The system may also include a holder that has at least one slot configured to contain the biological indicator and at least a third port connected to the first fluid-delivery component. The third port may be positioned at the base of the slot to mate with the first port. The holder may also include a fourth port disposed at the base of the slot. The fourth port may be positioned to mate with the second port. The holder may also include a window such that the biological indicator may be visible therethrough when disposed in the slot. The holder may further be connected to a sterilization tray disposed inside the sterilization chamber. A manifold may be connected to the sterilization tray such that the holder may be connected to the manifold. Further, the first fluid-delivery component may be connected to the manifold such that the manifold may be connected to the third port. The system may also include a second fluid delivery component connected to the manifold and at least partially disposed in the sterilization tray. Thus, the second fluid-delivery component may be connected to a lumen of an instrument, e.g., an endoscope, disposed in the sterilization tray. So configured, during a sterilization cycle, the interior of the biological indicator may contain a liquid-chemical sterilant that had previously been flowed through the endoscope.

In further embodiments, the holder may be disposed on an exterior surface of the sterilization system. Such a holder may further include a display screen. It may also include four or more slots for holding biological indicators.

BRIEF DESCRIPTION OF THE DRAWINGS

While the specification concludes with claims, which particularly point out and distinctly claim the subject matter described herein, it is believed the subject matter will be better understood from the following description of certain examples taken in conjunction with the accompanying drawings, in which like reference numerals identify the same elements and in which:

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Automated sterilization equipment and routines for endoscopes that employ a liquid-chemical sterilant, e.g., hydrogen peroxide or peracetic acid, are being developed to overcome certain shortcomings associated with sterilizing endoscopes using vapor-chemical sterilants. However, as with the vapor-based processes, development of a reliable technique for assessing whether the endoscope has been sterilized remains a challenge. Moreover, the biological indicators that are used in vapor-based processes are not suitable for use in liquid-based processes because such indicators are designed to have gaseous sterilant, but not liquid sterilant, removed therefrom. Thus, it would be advantageous to provide an indicator from which liquids may be readily removed and to which liquids may be readily introduced. Further, indicators for vapor-based processes typically require a user to break an ampule containing a growth medium and to transfer the indicator to an apparatus capable of incubating the indicator and detecting a change, such as a change in color or fluorescence of a growth medium in the indicator. When a liquid-chemical sterilant is used, precautions should be taken to avoid burns to the user that might result from residual liquid sterilant remaining on the indicator. Thus, it would be advantageous to provide a system capable of manipulating a biological indicator for use with a liquid-chemical sterilant that does not require user intervention. Proposed herein are devices and methods that may be used to determine whether an endoscope has been sterilized by a sterilization routine employing a liquid-chemical sterilant that further address these design inputs.

Figure 1:
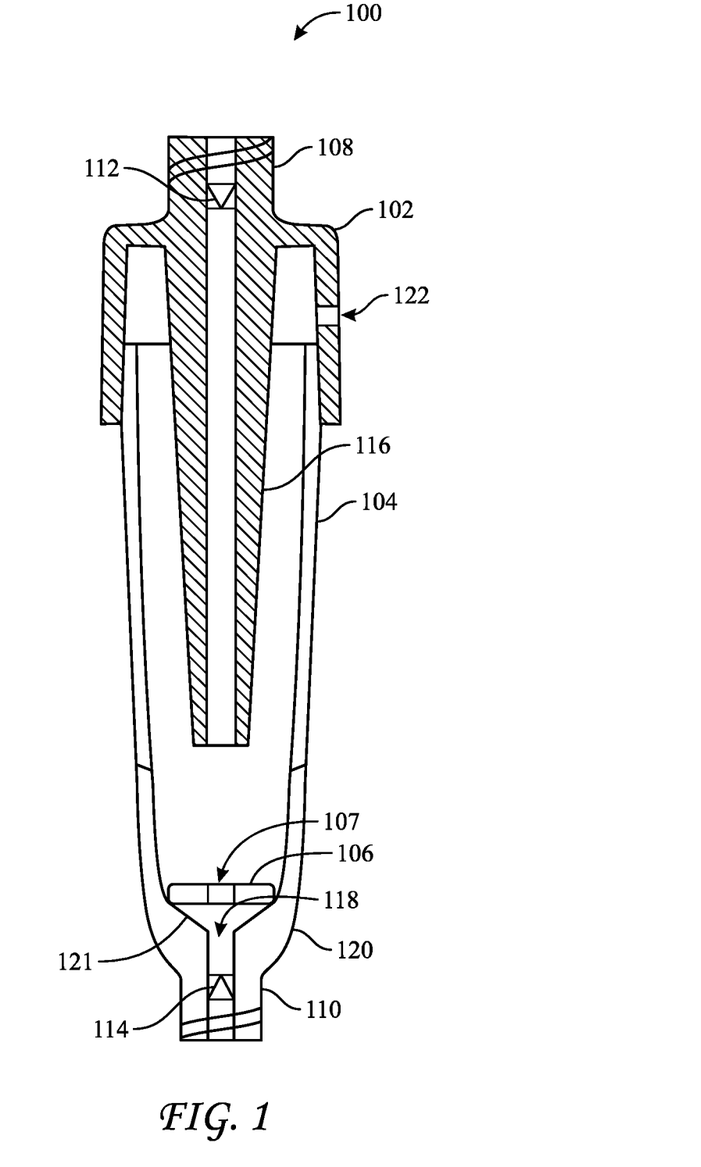
FIG. 1 depicts a side cross-section view of a first biological indicator suitable for use in a liquid-chemical sterilization process.

FIG. 1 reflects a biological indicator ("BI") 100 for use in an liquid-chemical sterilization procedure, particularly an automated liquid-chemical sterilization procedure conducted by a liquid-chemical sterilization apparatus having a chamber within which an instrument, e.g., a medical device, such as an endoscope may be placed. BI 100 includes a cap 102, a vial 104, and a carrier 106. Carrier 106 is disposed in vial 104, typically on or proximate to the bottom of vial 104. Cap 102 is disposed atop vial 104, preferably in a tight-fitting relationship, such as a friction fit or a press fit. For example, cap 102 may have an inner width or diameter that is equal to or slightly smaller than the outer width or diameter of vial 104. BI 100 further includes at least one port, e.g., Luer ports 108 and 110. As shown, Luer port 108 may be integrated into cap 102, whereas Luer port 110 may be integrated through a base of vial 104. Valves, e.g., valve 112 and valve 114, may be incorporated into Luer ports 108 and 110 to assist in regulating flow of liquids through the BI, typically in through port 108 and out through port 110 and preventing accidental removal of liquids therefrom. The valves may further assist in preventing contaminants from entering BI 100 after BI 100 has been subject to a sterilization cycle. Valves 112 and 114 may be one-way or two-way valves. For example, valve 112 may be a one-way valve, such as a duckbill valve, whereas valve 114 may be a two-way normally closed check valve that opens only when subject to forces imparted to it by an object inserted into it from outside the BI. For example, port 112 and valve 114 may be provided as a normally-closed check-valve, such as B. Braun Part No. 415062, which includes a female Luer port and which may be opened upon connection to a male Luer fitting. Ports 108 and 110 may additionally extend into vial 104. For example, port 108 includes a spout or extension 116 that extends deep into vial 104 such that fluids introduced therethrough are forced to flow over carrier 106 while submersing it. BI 100 may additionally include an exhaust port, such as port 122 through cap 102, which allows air to escape from the BI as liquid is introduced therein. FIG. 1 shows BI 100 in an open or uncompressed configuration. Cap 102 may be depressed relative to vial 104 to place BI 100 into a compressed configuration such that exhaust port may be become blocked or sealed by an outer wall of vial 104.

The portion of port 110 that extends into vial 104 includes an opening 118. Ideally, vial 100 does not include any empty space or voids beneath the level of opening 118 such that when the longitudinal axis of BI 100 is aligned with the direction of gravity and valve 114 is open, all liquids in vial 104 may flow readily through port 110 without any becoming trapped in the vial. Thus, a bottom portion 120 of vial 104 that is proximate to the portion of port 110 that extends into the vial may be provided as having an angled surface or declivity 121 directed toward opening 118 such that any liquid disposed on the declivity while valve 114 is open would flow out of vial 104 through opening 118 and port 104. In those embodiments that include declivity 121, carrier 106 may be disposed somewhat above opening 118 to prevent it from blocking opening 118. Further, carrier 106 and may include one or more voids or perforations 107 therethrough to assist liquid to flow therethrough and towards opening 118 such that it may flow out of BI 100 when valve 114 is open.

Carrier 106 may have the form of a disk and contain or be impregnated with a source of microorganisms, e.g., spores, or active enzymes. Carrier 106 may be disposed in vial 104. Spores from *Bacillus, Geobacillus*, and *Clostridia* species are often used to monitor sterilization processes using chemical sterilants. Accordingly, carrier 106 may be impregnated with spores from *Bacillus, Geobacillus*, and/or *Clostridia* species. For example, sterilization process resistant spores can include, but are not limited to, at least one of *Geobacillus stearothermophilus* spores, *Bacillus subtilis* spores, *Bacillus atrophaeus* spores, *Bacillus megaterium* spores, *Bacillus coagulans* spores, *Clostridium sporogenes* spores, *Bacillus pumilus* spores and combinations thereof.

Carrier 106 may be water-absorbent and may be formed of filter paper. Sheet-like materials such as cloth, nonwoven polypropylene, rayon or nylon, and microporous polymeric materials may also be used. Non-water absorbent materials are also appropriate for use, such as metals (e.g., aluminum or stainless steel), glass (e.g., glass beads or glass fibers), porcelain, or plastic. Additionally, carrier 110 can be constructed of a combination of the aforementioned materials. In some embodiments, carrier 110 may have a thickness of approximately 0.1 to 0.5 millimeters.

During use, carrier 106 becomes immersed in a growth medium. The growth medium may be introduced or flowed into the BI via port 108. Alternatively, as reflected in FIGS. 2-3, the growth medium may be contained in frangible ampule 224 such that a user may break the ampule, which causes the growth medium to submerge carrier 106. The growth medium should be capable of promoting growth of any viable microorganisms or other source of biological activity disposed on carrier 106. Preferably, the microorganisms are chosen to generate enzymes that interact with enzyme substrates of the growth medium to create a change in a visual characteristic of the growth medium, e.g., by causing a color change or fluorescence intensity change to the growth medium. Continued growth of the microorganisms in the growth medium causes an increase in the concentration of the detectable product in the growth medium. In certain embodiments, the detectable product is a fluorophore. Thus, an increase in concentration of the detectable product causes an increase in fluorescence. That is to say, the detectable product is detectable via changes in fluorescence intensity.

Enzymes and enzyme substrates that may be used to detect efficacy of a sterilization cycle are identified in U.S. Pat. No. 5,073,488, entitled "Rapid Method for Determining Efficacy of a Sterilization Cycle and Rapid Read-Out Biological Indicator," issued Dec. 17, 1991, the disclosure of which is incorporated by reference herein; U.S. Pat. No. 5,418,167, entitled "Rapid Read-Out Biological Indicator," issued May 23, 1995, the disclosure of which is incorporated by reference herein; U.S. Pat. No. 5,223,401, entitled "Rapid Read-Out Sterility Indicator," issued Jun. 29, 1993, the disclosure of which is incorporated by reference herein; and U.S. Pat. No. 9,322,046, entitled "Biological Sterilization Indicator," issued Apr. 26, 2016, the disclosure of which is incorporated by reference herein.

Suitable enzymes may include hydrolytic enzymes and/or enzymes derived from spore-forming microorganisms, such as *Bacillus subtilis*. Enzymes from spore-forming microorganisms that can be useful in exemplary biological indicators may include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase, fatty acid esterases and combinations thereof.

In some exemplary methods for determining efficacy of a sterilization cycle as disclosed herein, enzyme substrates are converted to detectable product. For instance, an enzyme substrate may be characterized by a first emission spectrum (e.g., a first fluorescent emission spectrum) and a detectable product may be characterized by a second emission spectrum (e.g., a second fluorescent emission spectrum).

In some exemplary methods for determining efficacy of a sterilization cycle as disclosed herein, suitable enzyme substrates of use may include fluorogenic enzyme substrates. Useful fluorogenic enzyme substrates may be selected from: fluorogenic 4-methylumbelliferyl derivatives (hydrolysable to 4-methylumbelliferone ("4-Mu"), derivatives of 7-amido-4-methyl-coumarin, diacetylfluorescein derivatives, fluorescamine and combinations thereof.

Exemplary 4-methylumbelliferyl derivatives may be selected from: 4-methylumbelliferyl-2-acetamido-4,6-O-benzylidene-2-deoxy-β-D-glucopyranoside, 4-methylumbelliferyl acetate, 4-methylumbelliferyl-N-acetyl-β-D-galactosaminide, 4-methylumbelliferyl-N-acetyl-α-D-glucosaminide, 4-methylumbelliferyl-N-acetyl-β-D-glucosaminide, 2'-(4-methylumbelliferyl)-α-D-N-acetyl neuraminic acid, 4-methylumbelliferyl α-L-arabinofuranoside, 4-methylumbelliferyl α-L-arabinoside, 4-methylumbelliferyl butyrate, 4-methylumbelliferyl 13-D-cellobioside, methylumbelliferyl β-D-N,N' diacetyl chitobioside, 4-methylumbelliferyl elaidate, 4-methylumbelliferyl β-D-fucoside, 4-methylumbelliferyl α-L-fucoside, 4-methylumbelliferyl β-L-fucoside, 4-methylumbelliferyl α-D-galactoside, 4-methylumbelliferyl β-D-galactoside, 4-methylumbelliferyl α-D-glucoside, 4-methylumbelliferyl β-D-glucoside, 4-methylumbelliferyl (3-D-glucuronide, 4-methylumbelliferyl p-guanidinobenzoate, 4-methylumbelliferyl heptanoate, 4-methylumbelliferyl α-D-mannopyranoside, 4-methylumbelliferyl β-D-mannopyranoside, 4-methylumbelliferyl oleate, 4-methylumbelliferyl palmitate, 4-methylumbelliferyl phosphate, 4-methylumbelliferyl propionate, 4-methylumbelliferyl stearate, 4-methylumbelliferyl sulfate, 4-methylumbelliferyl β-D-N,N,N"-triacetyl-chitotriose, 4-methylumbelliferyl 2,3,5-tri-o-benzoyl-α-L-arabinofuranoside, 4-methylumbelliferyl-p- trimethylammonium cinnamate chloride, 4-methylumbelliferyl β-D-xyloside and combinations thereof.

In certain embodiments, the fluorescent response may be based on the naturally occurring alpha-glucosidase enzyme found in the *Geobacillus stearothermophilus* spore coat, which contains the enzyme and which is believed to be important in the germination of *G. stearothermophilus*. Alpha-glucosidase may be used to hydrolyze the bond between the glucose and 4-methylumbelliferyl moieties of 4-methylumbelliferyl α-D-glucopyranoside (α-MUG). α-MUG is not fluorescent. However, following hydrolyzation and separation of the moieties, the 4-Methylumbelliferone (4-MU) product is fluorescent. 4-MU fluoresces when excited by an external energy source, such as a light source that emits light having a wavelength of between approximately 360 and 370 nanometers. So excited, 4-MU emits light having a wavelength of between approximately 440 and 460 nanometers. In certain embodiments, the light source emits light having a wavelength of approximately 365 nanometers and the 4-MU emits light having a wavelength of 450 nm. The fluorescence of 4-MU is pH dependent. For example, when excited by light having a wavelength of 365 nanometers, the intensity of the emitted light is highest at a pH of 10.3. The intensity decreases with pH until about a pH of 7. Below this pH the intensity becomes negligible.

Cap 102 and vial 104 may be fabricated from any suitable material, preferably a hard and inert plastic, such as polycarbonate. Ideally, at least vial 104 is transparent to facilitate monitoring the growth medium for a detectable change to color or fluorescence.

Figure 2:
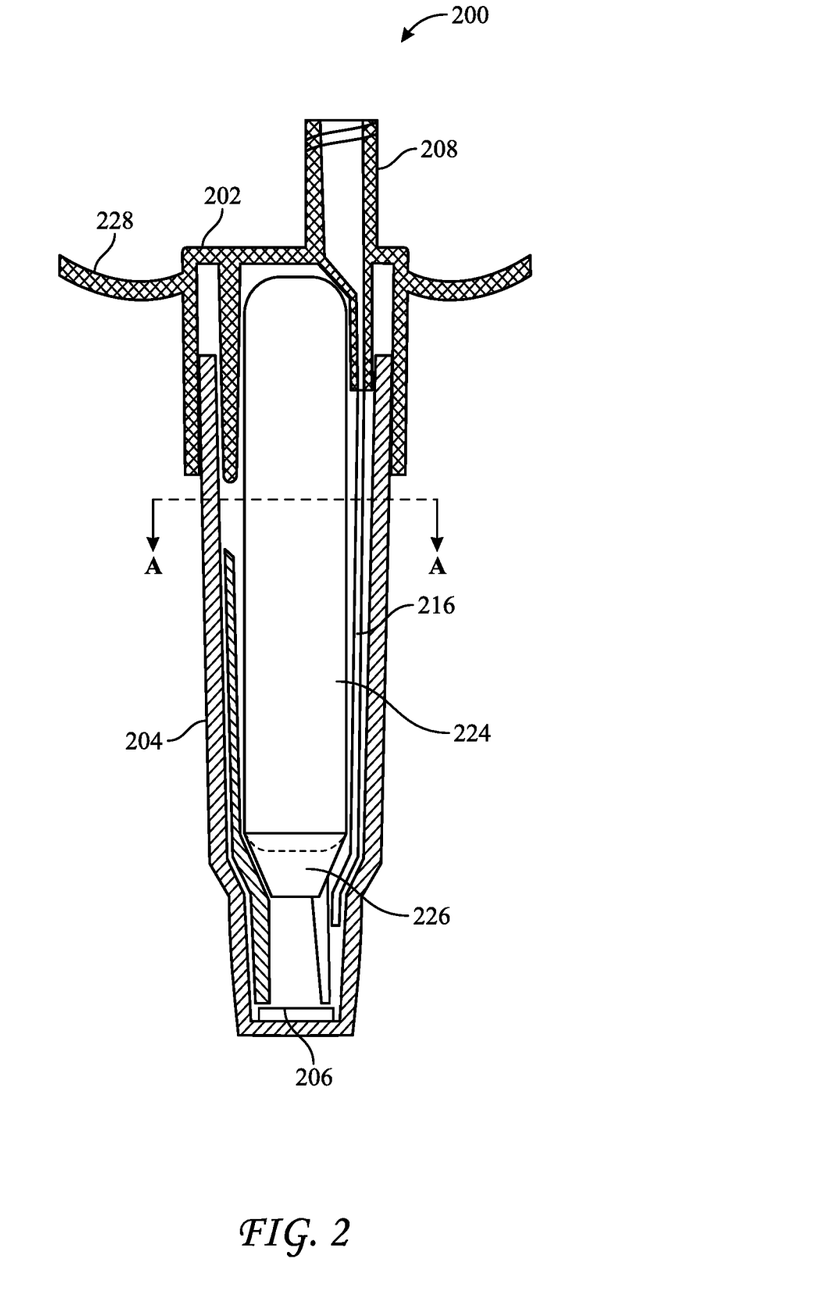
FIG. 2 depicts a side cross-section view of a second biological indicator suitable for use in a liquid-chemical sterilization process.
Figure 3:
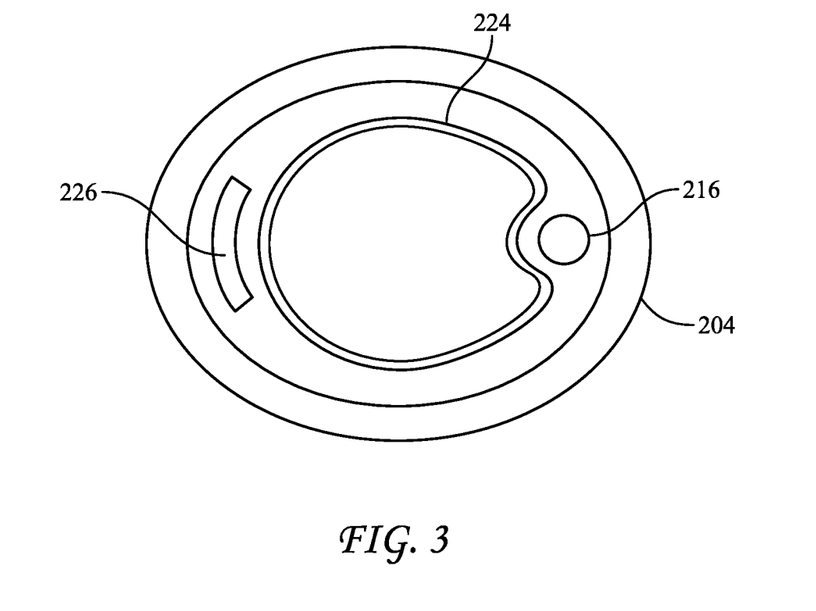
FIG. 3 depicts a top cross-section view the biological indicator of FIG. 2.

FIG. 2 reflects BI 200, which includes a cap 202, a vial 204, and a carrier 206 disposed within vial 204, preferably at or proximate to the base of vial 104. BI 200 further includes an ampule 224 disposed at least partially within vial 104 and in contact with insert 226. Ampule 224 may contain a growth medium, such as those described above, e.g., α-MUG. Insert 226 and cap 202 may further include features, such as stress concentrators, that may assist in breaking ampule 224, such as when cap 202 is depressed downward along vial 204, e.g., as explained in co-pending U.S. patent application Ser. Nos. 15/057,768 and 15/397,018, the disclosures of which are incorporated herein by reference in their entirety. Further, cap 202 may include one or more wings 228 extending therefrom, which may assist a user in providing compressive force between cap 202 and vial 204. As seen in FIG. 3, which is a cross-sectional top view of BI 200, ampule 224 may be provided having an irregular shape, such as an indented circular shape defining an indent, to provide a space in which to dispose pipette 216.

A port 208 may be integrated into and through cap 202. Port 208 may further include an extension, such as pipette 216, which may include a first end connected (e.g., bonded) to port 208, such that any liquid introduced through port 208 exits pipette 216 inside vial 204, somewhat removed from cap 202. As shown, pipette 216 includes a second end disposed proximate to the base of vial 204. Thus, liquids may be introduced and withdrawn from BI 200 via a single port. Preferably, sufficient space between the base of vial 204 and the second end of pipette 216 should sufficient such that upon depression of cap 202, the second end of pipette 216 should contact or nearly contact carrier 206. Furthermore, by inclusion of pipette 216, inclusion of ampule 224 in BI 200 is optional. That is, ampule 224 may be excluded from the BI 200 to allow for introduction of the growth medium into the BI via port 208 and pipette 216. In further embodiments not shown, a tube may be integrated into a sidewall of vial 204, extending from a location between cap 202 and carrier 206 to a location proximate to carrier 206. The second end of pipette 216 may be disposed within the tube such that upon depression of cap 202 relative to vial 204, the second end of pipette 216 may move toward carrier 206 within the tube. Thus, pipette 216 and the tube are provided as having a telescoping relationship. A seal, e.g., a gasket, may be provided between the two to ensure that the mate between pipette 216 and the tube is fluid tight. Accordingly, fluids may be delivered into and removed from vial 204 by way of the passage defined by pipette 216 and the tube integrated into the wall of vial 204.

Biological indicators used in vapor-based sterilization processes do not require features concerning fluid management, such as the ports, pipette, and valves described above, because vapor may be readily introduced and removed from inside the biological indicator by way of pressurizing and depressurizing a vacuum chamber in which the biological indicator and instruments are disposed during the process. Such features are required for biological indicators used in liquid based chemical sterilization procedures at least because sterilant, e.g., peracetic acid or hydrogen peroxide, must be introduced and removed therefrom. Further, when a neutralizer e.g., sodium metabisulfite or sodium bisulfite, is used to neutralize any sterilant remaining in the biological indicator, the neutralizer must be introduced and removed therefrom. Further, in those embodiments where the biological indicator does not include an ampule containing a growth medium, the growth medium must also be introduced into the biological indicator. Such fluid management steps may be facilitated by way of a biological indicator that is designed to be plumbed by a liquid-chemical sterilization system, which may further include an integrated incubator and reader akin to the Reader (ASP part no. 43220) of the commercially available STERRAD VELOCITY™ system, manufactured by applicant.

Figure 4:
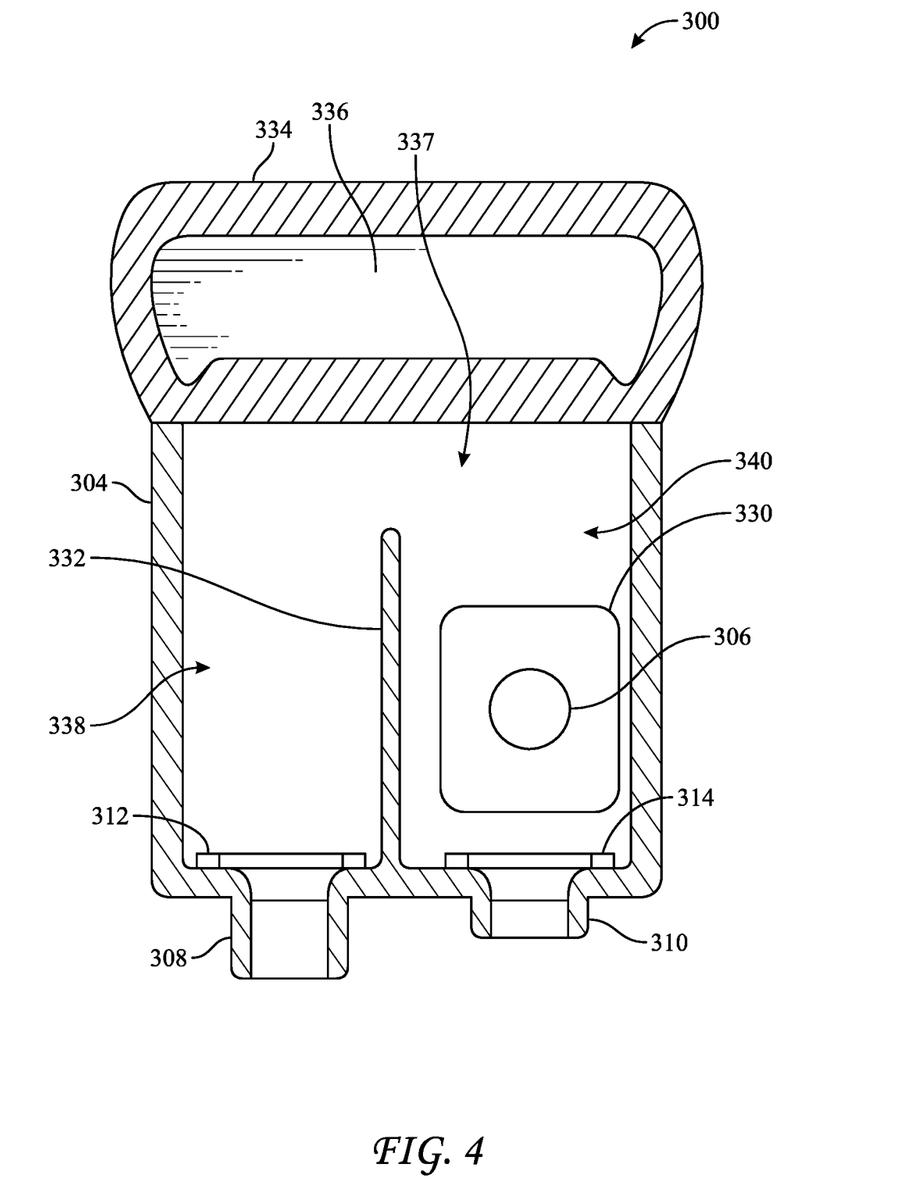
FIG. 4 depicts a side cross-section view of a third biological indicator suitable for use in a liquid-chemical sterilization process.

One such exemplary biological indicator, BI 300, is shown in FIG. 4. BI 300 includes a housing 304 defining an interior 337, a first port 308 including valve 312, a second port 310 including valve 314, and a carrier holder 330 containing a carrier 306. A divider 332 may be disposed between ports 308 and 310, extending into interior 337, to define two chambers, chamber 338 and chamber 340. As shown, carrier 306 is disposed in chamber 340. Ports 308 and 310 may be used as either an inlet port, and outlet port, or both. For example, a sterilant may be introduced into chamber 338 and then chamber 340 before being withdrawn through port 310. However, to minimize the amount of growth medium introduced, growth medium may be introduced to and withdrawn from chamber 340 via port 310, filling only chamber 340, such that port 308 is not used for flowing the growth medium. BI 300 may additionally include a handle 334, which might further include an indented portion 336 to assist a user to grip BI 300.

Figure 5:
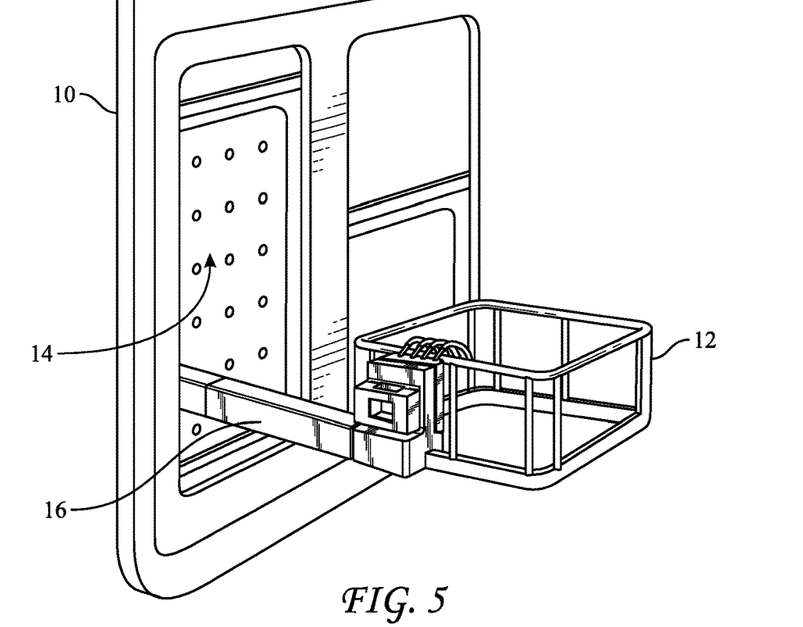
FIG. 5 depicts a schematic representation of a liquid-chemical sterilization system in an open configuration that includes features for assessing the biological indicator of FIG. 4.
Figure 6:
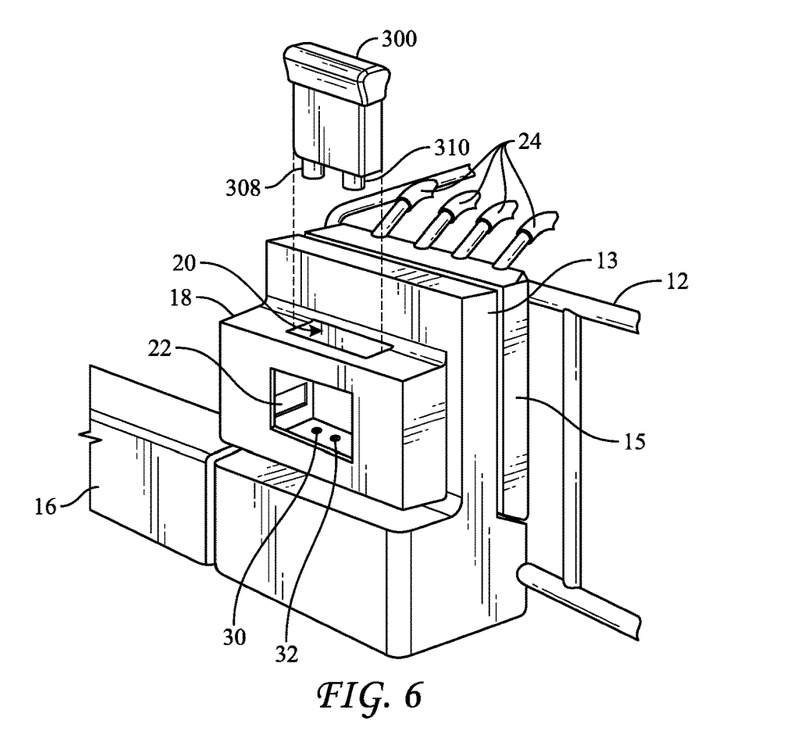
FIG. 6 is a close-up view of a portion of FIG. 5 showing the biological indicator of FIG. 4 aligned with a slot in a holder for receiving the biological indicator.
Figure 7:
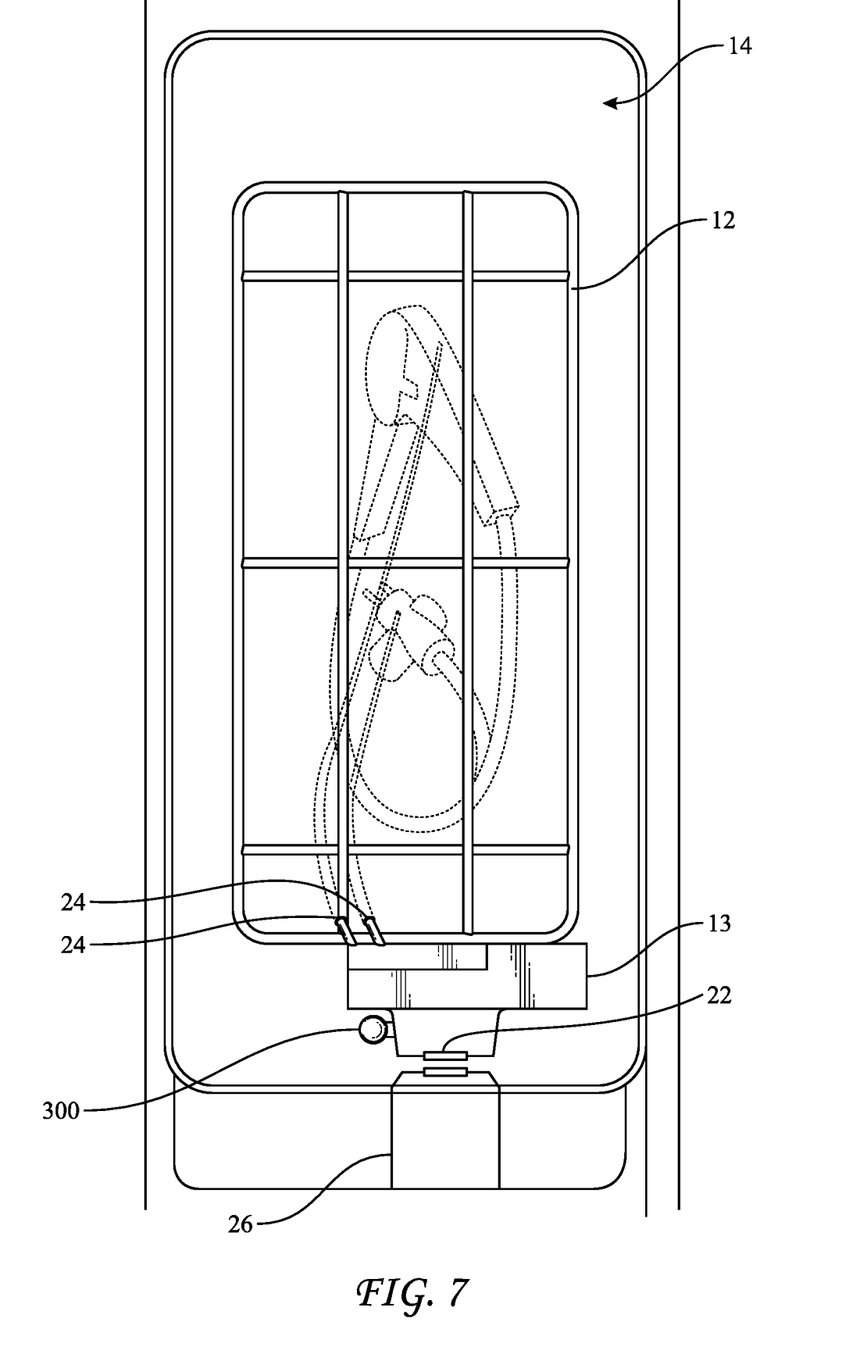
FIG. 7 is a schematic representation of the liquid-chemical sterilization system of FIG. 5 in a closed configuration.

FIGS. 5-7 show how BI 300 may be used in conjunction with a liquid-chemical sterilization system 10. System 10 includes a sterilization tray or basket 12 that is configured to be disposed either inside sterilization chamber 14 in a vertical position (FIG. 7) or outside of sterilization chamber 10 in a horizontal position (FIG. 5). Tray 12 may be maneuvered between the internal vertical and external horizontal position via articulating arm 16. Articulating arm may be hollow such that it can conduct liquids, such as sterilant, neutralizer, or growth medium therethrough by way of fluid delivery components, e.g., a common tube or multiple tubes with each tube being designated for one of the liquids.

Articulating arm mates to basket 12 and also to manifold 13. Additional fluid delivery components, e.g., tubes 24, extend out of manifold 13 and into basket 12, such that at least a portion of at least one of tubes 24, but preferably two tubes 24, are disposed in basket 12. Connection adapter 15 may help secure manifold 13 to basket 12 and provide only sterilant to the endoscope via tubes 24. Tubes 24 may be connected to lumens of an instrument to be sterilized while disposed in basket 12 and inside chamber 14. For example, tubes 24 may be connected to various ports, tubes, or other components of the endoscope (FIG. 7) such that sterilant may be flowed through the lumens of the endoscope during the sterilization procedure. As such, a volume of the sterilant that flows through the endoscope may be introduced into BI 300.

A holder 18 containing a slot 20 in which BI 300 may be disposed is attached to tray manifold 13. That is, slot 20 is configured to contain the biological indicator. Holder 18 also includes a window 22 through which BI 300 may be interrogated by a reading device 26 (FIG. 7) to assess a detectable change in color or fluorescence of the growth medium in BI 300. The reading device may be disposed at least partially within chamber 14 or outside but adjacent to chamber 14, but still within the sterilization system. At least one port, e.g., two ports—ports 30 and 32—may be disposed at the base of slot 20 and may mate, respectively, to ports 308 and 310 of BI 300. Thus, liquids may be delivered from sources of liquids (e.g., a source of liquid-chemical sterilant or a source of neutralizer) within system 10, e.g., under pressures generated by a pump, through articulating arm 16, manifold 13, holder 18 and to BI 300, via port 308 or 310. Liquids may also be removed from BI 300 in a reverse direction. In further embodiments, holder 18 also includes heating elements that may be used to incubate BI 300 at a temperature between approximately 50° C. and approximately 60° C., such as approximately 57° C., e.g., while the growth medium is contained in chamber 340 of BI 300.

As seen in FIG. 7, when tray 12 is disposed inside chamber 14 in a vertical position, window 22 on holder 18 aligns with a reading device 26 of liquid chemical sterilization system 10 such that BI 300 may be interrogated during the cycle to assess sterility of BI 300 and any other devices inside of chamber 14, e g., to determine whether the sterilization cycle may be ended.

Figure 8:
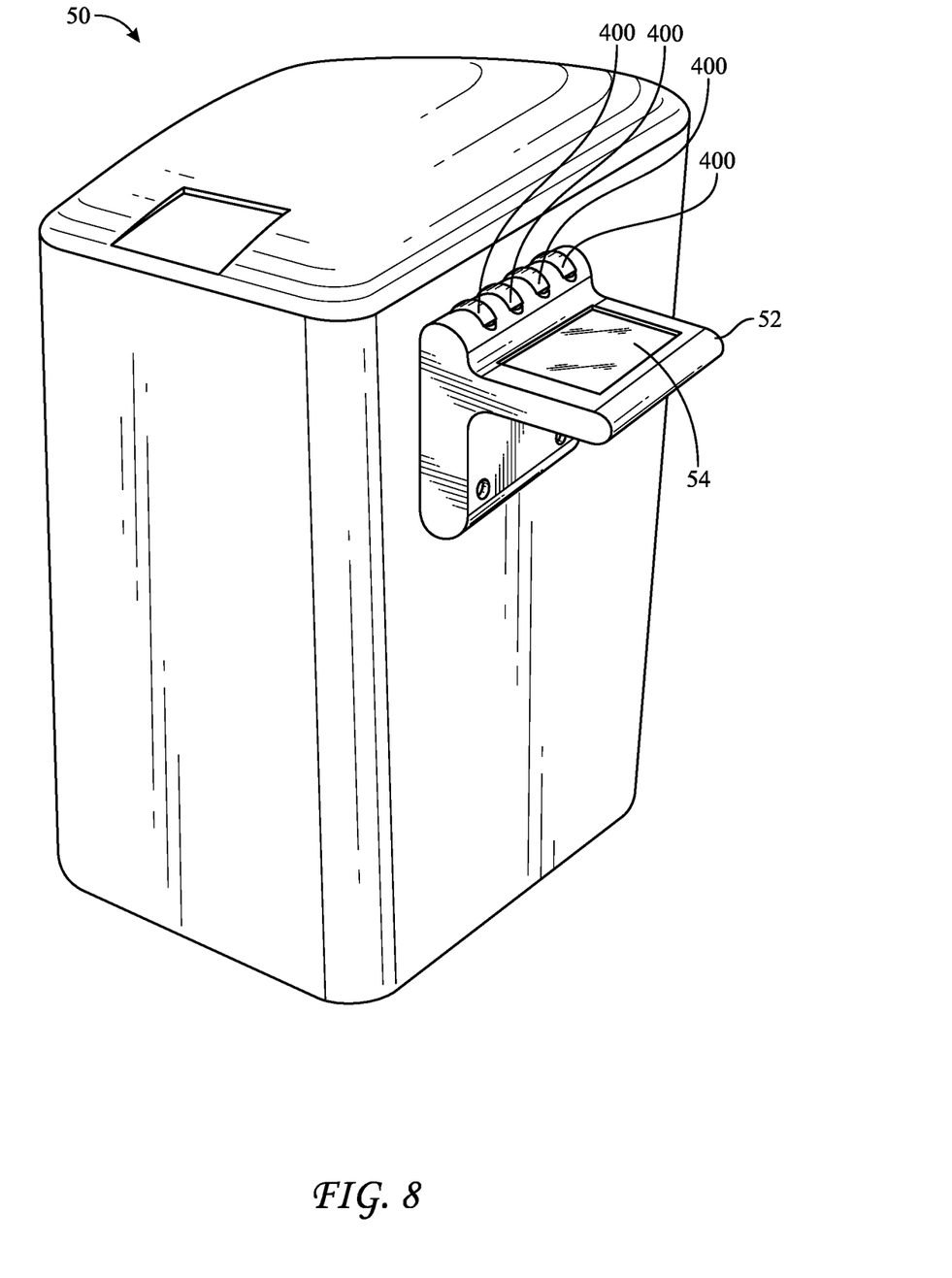
FIG. 8 is a schematic representation of another liquid-chemical sterilization system including a reading device.
Figure 9:
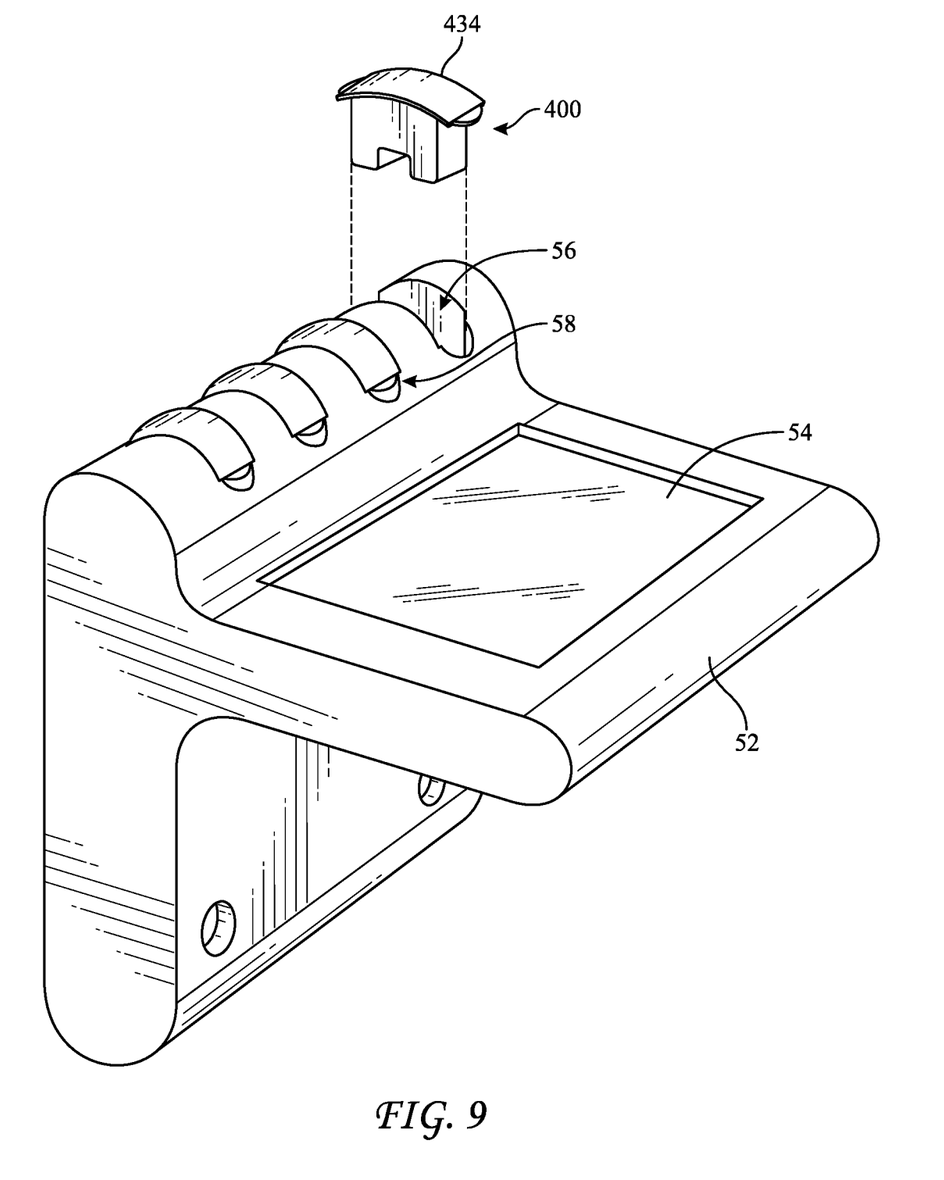
FIG. 9 is a close-up view of the reading device of FIG. 8.

FIG. 8 reflects a top-loading liquid-chemical sterilization system 50 that incorporates an external holder 52 configured to contain at least one BI 400, such as four BIs 400. Holder 52 may include heating elements for incubating BIs 400, fluidic connections for introducing and removing liquids such as sterilant, neutralizer, and a growth medium to BI 400, and light emitters and detectors capable of interrogating BI 400 for a change to color or fluorescence intensity. Holder 52 may further include a user interface, such as screen 54, which may be a touchscreen capable of accepting inputs from a user. As seen in FIG. 9, a BI 400 may be inserted and removed from holder 52. BI 400 may include a grip 434 that fits into a slot 56 such that a small space 58 is left between grip 434 and holder 52, which may facilitate removal of BI 400 therefrom. Because multiple BIs 400 may be placed into holder 52, these multiple BIs may each be interrogated to provide an indication of sterility for a single sterilization cycle. As such, the BIs may be compared to each other, as a control, to confirm that they provide similar results. As such, when one or more BIs provides an indication of sterility different than one or more of the others, the system may alert a user via screen 54 to perform further analysis or to subject the instruments to another sterilization cycle.

Figure 10A:
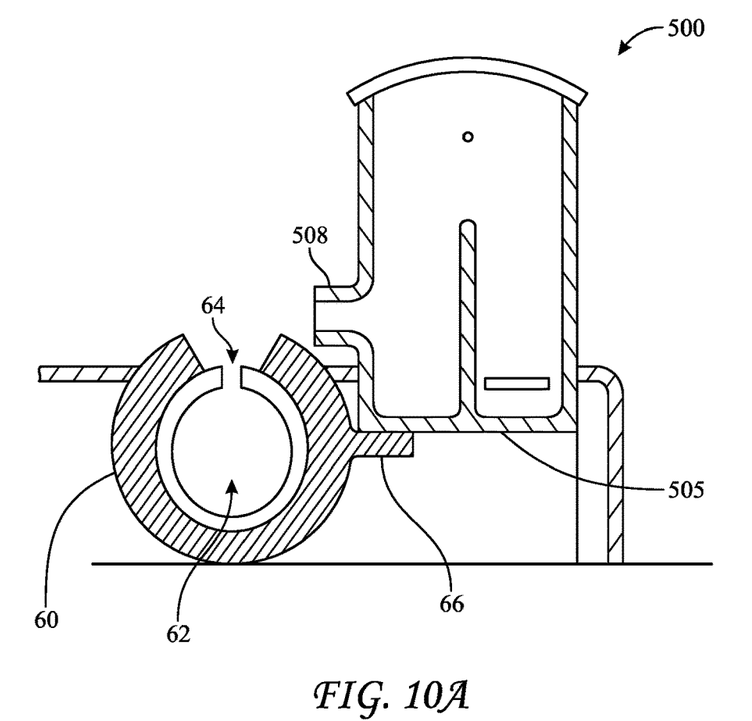
FIG. 10A is a schematic representation of a fourth biological indicator adjacent to a filling mechanism prior to filling.
Figure 10B:
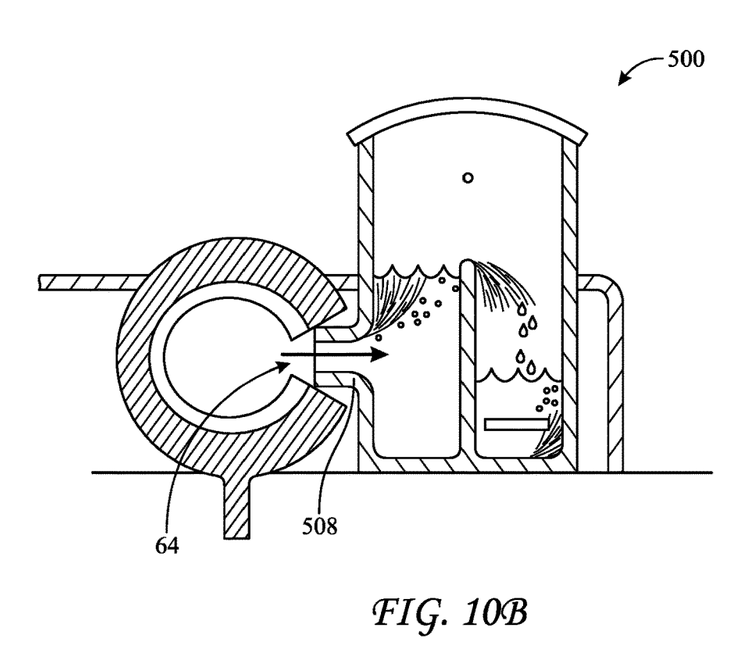
FIG. 10B is a schematic representation of a fourth biological indicator adjacent to a filling mechanism during filling.

A technique for delivering liquids to a BI 500 is reflected in FIGS. 10A and 10B. BI 500 includes a port 508 and a base 505. Filling mechanism 60 includes a reservoir of liquid 62, an opening 64, and an arm 66. BI 500 may be moved downward, such that base 505 contacts arm 66, causing filling mechanism 60 to rotate. As BI 500 is moved further downward, opening 64 rotates onto port 508 as arm 66 rotates out of contact with base 505. Further downward motion of BI 500 continues rotation of mechanism 500 under forces imparted thereto by port 508. As port 508 descends lower than a portion of reservoir 62, liquid may flow out of opening 64, through port 508, and into BI 500.

Figure 11:
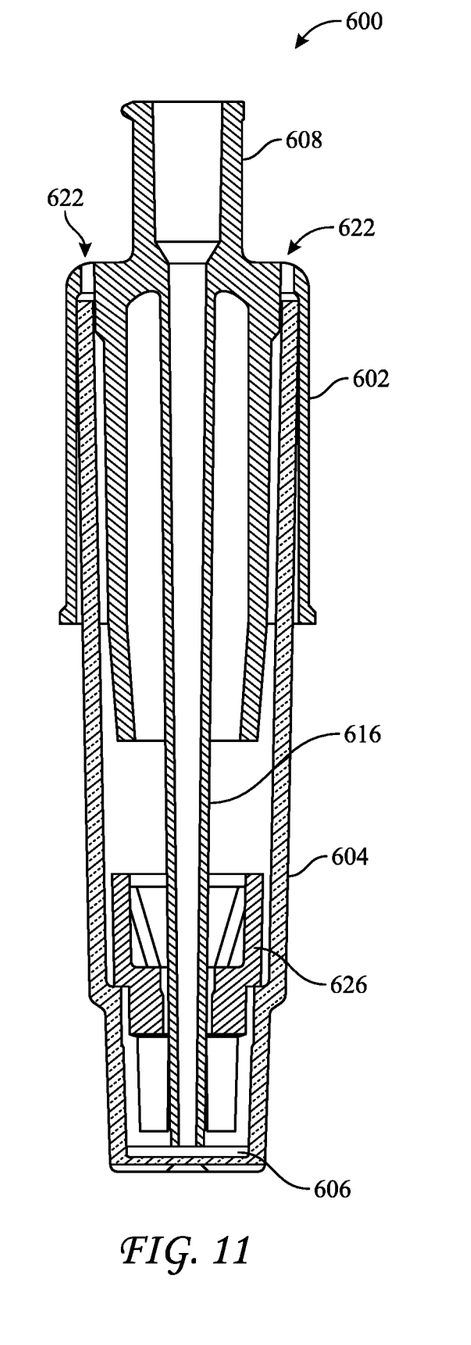
FIG. 11 depicts a side cross-section view of a fourth biological indicator suitable for use in a liquid-chemical sterilization process.

FIG. 11 reflects BI 600, which includes a cap 602, a vial 604, a carrier 606, and an insert 626. Cap 602 includes a spout or extension 616 that extends deep into vial 604 such that fluids introduced therethrough are forced to flow over carrier 606 while submersing it. Extension may extend through insert 626, which in this embodiment may assist in maintaining the position of carrier 606 at the base of vial 604, particularly during transportation. As shown, BI 600 does not include a growth medium provided in an ampule. Further, BI 600 includes a single port 608, which is integrated into cap 602. Accordingly, port 608 may be used to introduce and withdraw liquids from vial 604. BI 600 may be provided in an open or uncompressed configuration, similar to that of FIG. 1, where cap 602 is mated to vial 604 such that a gas, e.g., air or a sterilant, may flow into or out of vial 604 through vents 622. For example, air within vial 604 may be displaced out of BI 600 through vents 622 when introducing a liquid-chemical sterilant into vial 604 via spout 616. Further, in the open or uncompressed configuration, the bottom surface of spout 616 is displaced somewhat from carrier 606 to allow fluids may be readily introduced into vial 604 through spout 616. FIG. 11 reflects BI 600 in a compressed configuration in which vent ports 622 are blocked by portions of vial 604 and in which a bottom surface of spout 616 is disposed proximate to or in contact with carrier 606. Because vents 622 are blocked, flow of gas therethrough is restricted, which minimizes the likelihood of contaminants entering vial 604 post sterilization. Typically, BI 600 is sterilized in the open or uncompressed configuration. After sterilization, cap 602 may be depressed relative to vial 604 to place BI 600 into the compressed configuration for further analysis.

Any of the examples or embodiments described herein may include various other features in addition to or in lieu of those described above. The teachings, expressions, embodiments, examples, etc., described herein should not be viewed in isolation relative to each other. Various suitable ways in which the teachings herein may be combined should be clear to those skilled in the art in view of the teachings herein.

Having shown and described exemplary embodiments of the subject matter contained herein, further adaptations of the methods and systems described herein may be accomplished by appropriate modifications without departing from the scope of the claims. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well. Some such modifications should be apparent to those skilled in the art. For instance, the examples, embodiments, geometrics, materials, dimensions, ratios, steps, and the like discussed above are illustrative. Accordingly, the claims should not be limited to the specific details of structure and operation set forth in the written description and drawings.

We claim:

1. A liquid-chemical sterilization system, comprising:
a biological indicator, comprising
a housing defining an interior and including a first port having a first valve and a second port having a second valve,
a divider wall disposed within the interior, between the first port and the second port, defining two chambers, and
a carrier impregnated with microorganisms disposed in one of the two chambers;
a source of a liquid-chemical sterilant;
a first fluid-delivery component connected to the source of the liquid-chemical sterilant; and
a holder including
at least one slot configured to contain the biological indicator, and
at least a third port connected to the first fluid-delivery component and positioned at a base of the slot to mate with the first port.

2. The liquid-chemical sterilization system of claim 1, wherein the holder includes a fourth port disposed at the base of the slot positioned to mate with the second port.

3. The liquid-chemical sterilization system of claim 1, wherein the holder includes a window.

4. The liquid-chemical sterilization system of claim 3, wherein the holder is connected to a sterilization tray disposed inside a sterilization chamber.

5. The liquid-chemical sterilization system of claim 4, wherein a manifold is connected to the sterilization tray and the holder is connected to the manifold.

6. The liquid-chemical sterilization system of claim 5, wherein the first fluid delivery component is connected to the manifold and the manifold is connected to the third port.

7. The liquid-chemical sterilization system of claim 6, further comprising a second fluid delivery component connected to the manifold and at least partially disposed in the sterilization tray.

8. The liquid-chemical sterilization system of claim 7, wherein the second fluid delivery component is connected to a lumen of an instrument disposed in the sterilization tray.

9. The liquid-chemical sterilization system of claim 8, wherein the instrument comprises an endoscope.

10. The liquid-chemical sterilization system of claim 9, wherein the interior of the biological indicator contains a liquid-chemical sterilant that had previously been flowed through the endoscope.

11. The liquid-chemical sterilization system of claim 10, wherein a volume of liquid chemical sterilant that had previously been flowed through the endoscope is disposed in the interior of the biological indicator.

12. The liquid-chemical sterilization system of claim 2, wherein the holder is disposed on an exterior surface of the sterilization system.

13. The liquid-chemical sterilization system of claim 12, wherein the holder includes a screen.

14. The liquid-chemical sterilization system of claim 13, wherein the holder includes four slots.

15. The liquid-chemical sterilization system of claim 14, wherein each slot contains a different biological indicator.

* * * * *